United States Patent [19]

Armington

[11] Patent Number: 4,893,632

[45] Date of Patent: Jan. 16, 1990

[54] METHOD AND APPARATUS FOR COMPARING WAVEFORM SHAPES OF TIME-VARYING SIGNALS

[75] Inventor: Robert M. Armington, West Peabody, Mass.

[73] Assignee: Siemens Aktiengesellschaft, Berlin and Munich, Fed. Rep. of Germany

[21] Appl. No.: 181,027

[22] Filed: Apr. 13, 1988

[51] Int. Cl.$^4$ .............................................. A61B 5/04
[52] U.S. Cl. ..................................... 128/696; 128/708
[58] Field of Search .............. 128/696, 702, 706, 708; 364/413.05, 413.06

[56] References Cited

U.S. PATENT DOCUMENTS

| | | | |
|---|---|---|---|
| 3,829,766 | 8/1974 | Herz | 324/77 R |
| 4,023,564 | 5/1977 | Valiquette et al. | 128/2.06 A |
| 4,492,235 | 1/1985 | Sitrick | 128/705 |
| 4,680,708 | 7/1987 | Ambos et al. | 364/417 |
| 4,732,158 | 3/1988 | Sadeh | 128/702 |
| 4,736,295 | 4/1988 | Lachivev et al. | 364/413.06 |
| 4,742,458 | 5/1988 | Nathans et al. | 128/702 |

Primary Examiner—Francis Jaworski
Assistant Examiner—George Manuel
Attorney, Agent, or Firm—Lawrence C. Edelman

[57] ABSTRACT

A method and apparatus for comparing waveshape portions of at least one time-varying signal by first forming initial templates of digital signal samples representative of the amplitude of successive time-spaced samples of portions of the time-varying signal. Next, forming reduced templates having a number of digital signal elements which is less than the number of samples in corresponding ones of the initial templates, each element of the reduced template comprising a combination of at least two samples from its corresponding initial template. And then processing corresponding elements of at least two of the reduced templates for deriving a signal representative of the degree of similarity of the respective portions of the time-varying signal represented by at least two reduced templates.

15 Claims, 2 Drawing Sheets

METHOD AND APPARATUS FOR COMPARING WAVEFORM SHAPES OF TIME-VARYING SIGNALS

BACKGROUND OF THE INVENTION

1. Field of the Invention

The present invention relates generally to waveshape monitoring devices, and more particularly to a method and apparatus for comparing electrocardiogram waveshapes.

2. Description of the Prior Art

Waveshape monitoring devices typically detect particular waveshape portions of a more generalized time-varying signal having a variety of waveshapes. Particular use for such devices is found in heart monitoring equipment, such as arrhythmia detectors. One common form of waveshape detection generally used in arrhythmias detectors compares portions of an input waveform to a stored waveform. In this type of comparison, a portion of the input waveform is stored as a template comprising a group of time sequential amplitude values representative of the values of successive amplitudes of the signal portion which is to be detected. The initial signal portion detected and used for forming the template may be visually selected by the operator of the monitoring equipment. Thereafter, successive groups of time-sequential amplitude values of the input waveform are sequentially compared to the stored template values during the monitoring of the input waveform by the monitor. If a correlation greater than a predetermined confidence level is found, a signal is generated which indicates the input waveshape portion matches the stored template.

In the field of arrhythmia monitoring, QRS complexes of an electrocardiogram (ECG) signal are analyzed to determine whether they are atrial or ventricular in origin. A common technique used to classify QRS complexes is to compare them to other QRS complexes stored in templates which have already been classified. Correlation is frequently used to determine the degree of similarity between two QRS complexes. Correlation is performed on a reference complex x1 and a candidate complex x2 according to the following equation:

$$r = \frac{\sum\limits_{i=1}^{N}(x1_i - \overline{x1})*(x2_i - \overline{x2})}{\sqrt{\sum\limits_{i=1}^{N}(x1_i - \overline{x1})^2 * \sum\limits_{i=1}^{N}(x2_i - \overline{x2})^2}}$$

where $\overline{x1} = \frac{1}{N}\sum\limits_{i=1}^{N} x1_i$ and $\overline{x2} = \frac{1}{N}\sum\limits_{i=1}^{N} x2_i$ = mean value If the correlation coefficient r is greater than a fixed limit, e.g., 0.98, then the candidate complex is classified the same as the template that is matched.

One of the problems with this technique is that it is computationally demanding because of the number of multiplications and divisions which are required for determining the correlation coefficient. This problem is compounded because correlation is typically performed on many templates before a match can be determined. For example, the monitoring equipment may include not only stored templates for various portions of the ECG signal but also recurrent variations of specific portions, e.g., recurrent variations of the QRS complex. Furthermore, it may be desirable to compare entire QRS complexes including the T wave; however, because correlation requires considerable processing, many systems only use the QRS complex for correlation purposes in order to reduce the amount of required computations. An additional problem with correlation is that it is sensitive to misalignment of the QRS fiducial point.

An object of the present invention is to simplify the waveshape comparing process by reducing the number of samples stored in the template, thereby reducing the number of computations which must be performed. A further object of the invention is to reduce the complexity of the computations which are required to be performed in order to rapidly accomplish a reliable comparison between waveshapes using uncomplicated means.

SUMMARY OF THE INVENTION

In its broadest aspect, the invention comprises a method and apparatus for sampling portions of an input waveform and modifying samples of an original template for making and storing a reduced template. Each element of the reduced template is formed from a combination of at least two samples of a original template. This, in effect, encodes additional information into each element of the reduced template. Successive portions of the input waveform are processed in the same manner as the samples of the original template to form signal elements of candidate templates which are then compared with previously stored reduced templates for determining a match of the stored and candidate templates.

Since each of the elements of either of the stored reduced template or the candidate template are formed from at least two of the original samples, the character of the waveshape information contained in each element is different from the original samples in that it has information from a plurality of original samples encoded therein. The inventor has found that a simpler and faster computation can be performed using these elements for matching waveshapes, as compared with the computations required for achieving a similar confidence level of a match using the original samples, as is typically done using correlation.

In a preferred embodiment, a waveshape detector comprises means for establishing an original template of time sequential amplitude values representative of the waveshape of a desired portion of a time-varying signal to be analyzed, means for normalizing the amplitude values of the original template, means for combining groups of at least two of said normalized amplitude values of said original template for forming elements of a reduced template. Thereafter, successive groups of amplitude samples of the time varying input signal are similarly combined for forming successive candidate reduced templates. The elements of the successive candidate templates are compared to the elements of the first reduced template by simple addition and/or subtraction processing for determining matched waveshapes.

Other features and advantages of the invention will be apparent from the description of the preferred embodiment and from the claims.

For a fuller understanding of the present invention, reference should now be made to the following detailed description of the preferred embodiment of the invention and to the accompanying drawings.

DETAILED DESCRIPTION OF THE PREFERRED EMBODIMENTS

Figure 1:
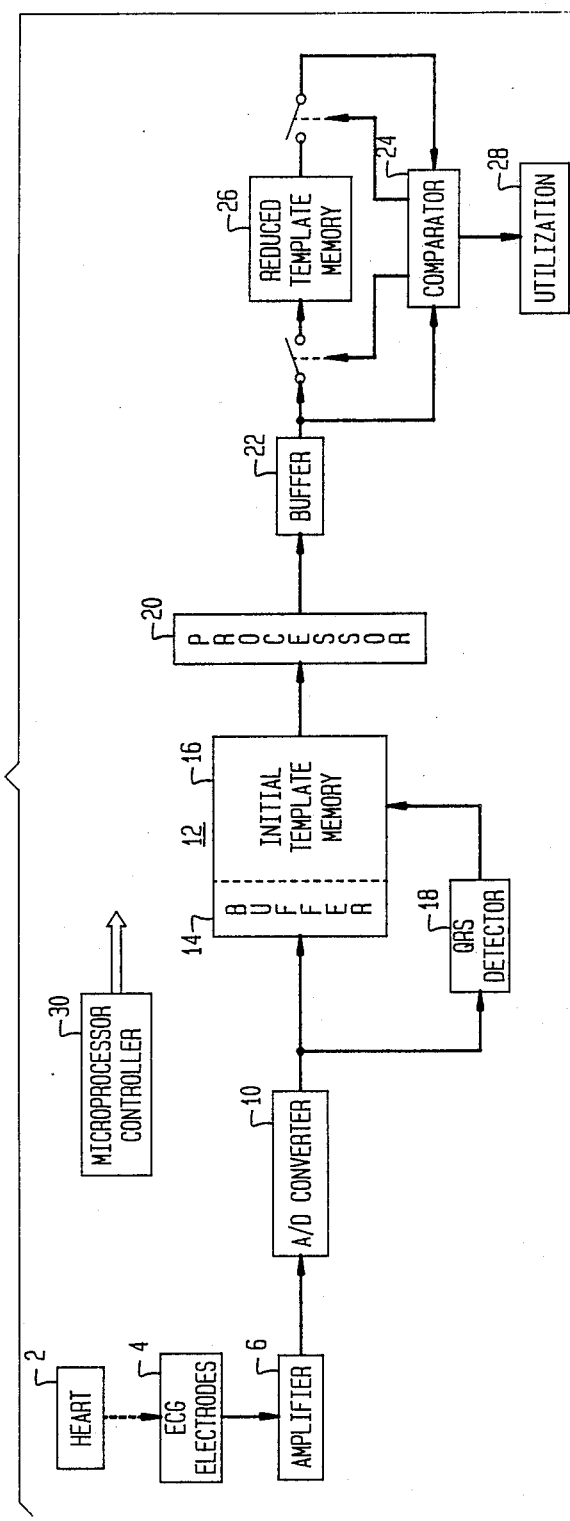
FIG. 1 illustrates in functional block diagram form a heart monitor constructed in accordance with the principles of the invention.
Figure 2:
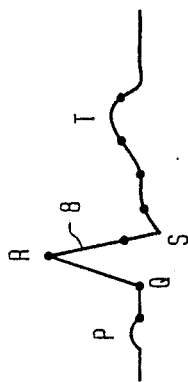
FIG. 2 illustrates a typical ECG waveform.

The waveshape monitor of the invention is illustrated in FIG. 1 as a cardiac arrhythmia monitor. Electrical signals generated by expansion and contraction of muscles of the heart 2 of a patient (not shown) are sensed in a conventional manner by electrocardiogram (ECG) electrodes 4. A conventional ECG amplifier 6 filters, amplifies and combines the electrical signals sensed by ECG electrodes 4 and generates at its output a time-varying signal representative of the electrical activity of heart 2. The time-varying waveform 8 of FIG. 2 illustrates a single heartbeat portion of a normal adult ECG. A typical ECG waveform comprises a P wave of positive polarity, a QRS complex consisting of a negative Q wave, a positive R wave, a negative S wave, and a positive polarity T wave. The R wave is usually the most prominent portion of the ECG signal.

In a conventional manner, an analog-to-digital (A/D) converter 10 samples ECG waveform 8 and provides at its output successive digital representations of the amplitude of waveform 8 at e.g., a 400 Hz rate. A memory 12 includes a buffer portion 14 which receives the digital signals from A/D converter 10 and stores digital representations for 300 millisecond portions of the ECG waveform.

At the same time, a QRS detector 18 detects QRS complexes in a conventional manner, such as by detecting the peaks of the ECG waveform, which as shown by waveform 8 of FIG. 2, corresponds to the peak of the R wave. In this manner, the output of QRS detector 18 is used to control the flow of digital representations from buffer 14 into an initial template memory 16. In the preferred embodiment, initial template memory 16 sequentially stores initial templates so that one digital amplitude sample of each QRS complex corresponds with the peak of the R wave, two samples are provided before this peak and five samples are provided after this peak. Each of these eight samples is spaced 50 milliseconds from its adjacent sample. These eight samples are illustrated as dots in waveform 8 of FIG. 2 and are representative of a single initial template. While each initial template is stored in initial template memory 16 and then processed, another portion of buffer 14 is being utilized for storing the next 300 millisecond portion of the ECG signal.

In accordance with the principles of the invention, the initial templates representative of the QRS complexes are processed further to form reduced templates having a reduced number of elements. More specifically, a processor 20 first normalizes the samples of the initial template stored in memory 16. This is done to eliminate the affect of QRS amplitude variations on later processing stages. In the preferred embodiment, normalization is accomplished by assigning to the largest sample amplitude value of the initially stored templates, the value 16 and assigning to the smallest sample amplitude value, the value zero. This process makes it possible to represent each sample of the reduced template as a four-bit word. For example, if an initial template was as follows:

$$x = [0, 0, 100, 10, 0, 2, 15, 30]$$

the normalized template would be:

$$x = [0, 0, 16, 1, 0, 0, 2, 4].$$

Thereafter, each element of the reduced template is formed by combining selected ones of the samples of the normalized template. In the preferred embodiment, the combining is accomplished by processor 20 according to the following equation:

$$y[i] = \sum_{i=0}^{3} x[i] - x[i+4]$$

In accordance with this equation, the first reduced template would be as follows:

$$y = [0, 0, 14, -3]$$

and these four digital values would be temporarily stored in a buffer memory 22. A comparator 24 compares the templates stored in buffer memory 22 to those already stored in a reduced template memory 26. If no match is found, as will be the case for the first reduced template, that template is transferred out of buffer memory 22 and stored in a first template location in memory 26. Memory 26 has sufficient memory locations and input/output multiplexing (not shown) for storing a plurality of reduced templates.

The next QRS complex is similarly processed by components 4–20 and presented by buffer 22 as candidates for storage in reduced template memory 26. Comparator 24 examines each candidate template by sequentially comparing it to previously stored templates in memory 26. If the candidate is considered to be the same, e.g., "a match", with a stored template, their digital values are averaged in order that comparable waveshape portions can track slowly occurring small changes in overall waveshape. If the templates do not match, the candidate template is stored as a new reduced template in reduced template memory 26. Comparator 24 also compares measured features relating to the candidate and stored templates, as will be described in greater detail later on.

Since each reduced template has half as many elements as those of the initial template, less memory space is needed for storing the reduced templates. Furthermore, due to the combining of samples in the initial template for forming each element of the reduced template, the inventor has found that simplified comparison processing can be used to determine if there is a match, as compared with conventional signal correlation techniques. In the preferred embodiment, each candidate reduced template is compared with the stored templates in accordance with the following equation which is a measure of similarity between the templates:

$$s = \sum_{i=0}^{3} |y1[i] - y2[i]|$$

If the value of s is less than a certain threshold, than the templates are considered a match.

This type of comparison is advantageous over the prior art technique, since it is much less computationally demanding in that relatively few simple subtractions are required, as compared with conventional signal correlation techniques. Due to the simplified waveshape comparison method and apparatus of the present invention, a great many more templates can be stored, compared and classified, and at a lower cost as compared with conventional prior art heart monitors. Additionally, a greater portion of the ECG signal can be processed, for example by including portions of the T wave portion, at very little extra cost in circuit complexity.

A utilization means 28 uses the information stored in reduced template 22 for providing useful heart monitoring indications. For example, in a preferred embodiment, utilization means 28 includes a preprogrammed list of feature classifications and, in conjunction with comparator 24 classifies the reduced templates into predetermined classes. Such classification can be based upon measurement of various QRS features, e.g., time intervals between various portions of the QRS complex, their relative amplitude values and their frequency of occurence. Once the templates are classified, a rhythm detector (not shown) within utilization means 28 examines them for abnormal patterns or sequences of occurrence in order to indicate the condition of heart 2. For example, the rhythm detector of utilization means 28 may be programmed to trigger an alarm if two consecutive premature ventricular beats (a couplet) is detected. A microprocessor controller 30 provides the necessary control signals for operation of the FIG. 1 arrangement.

Figure 3:
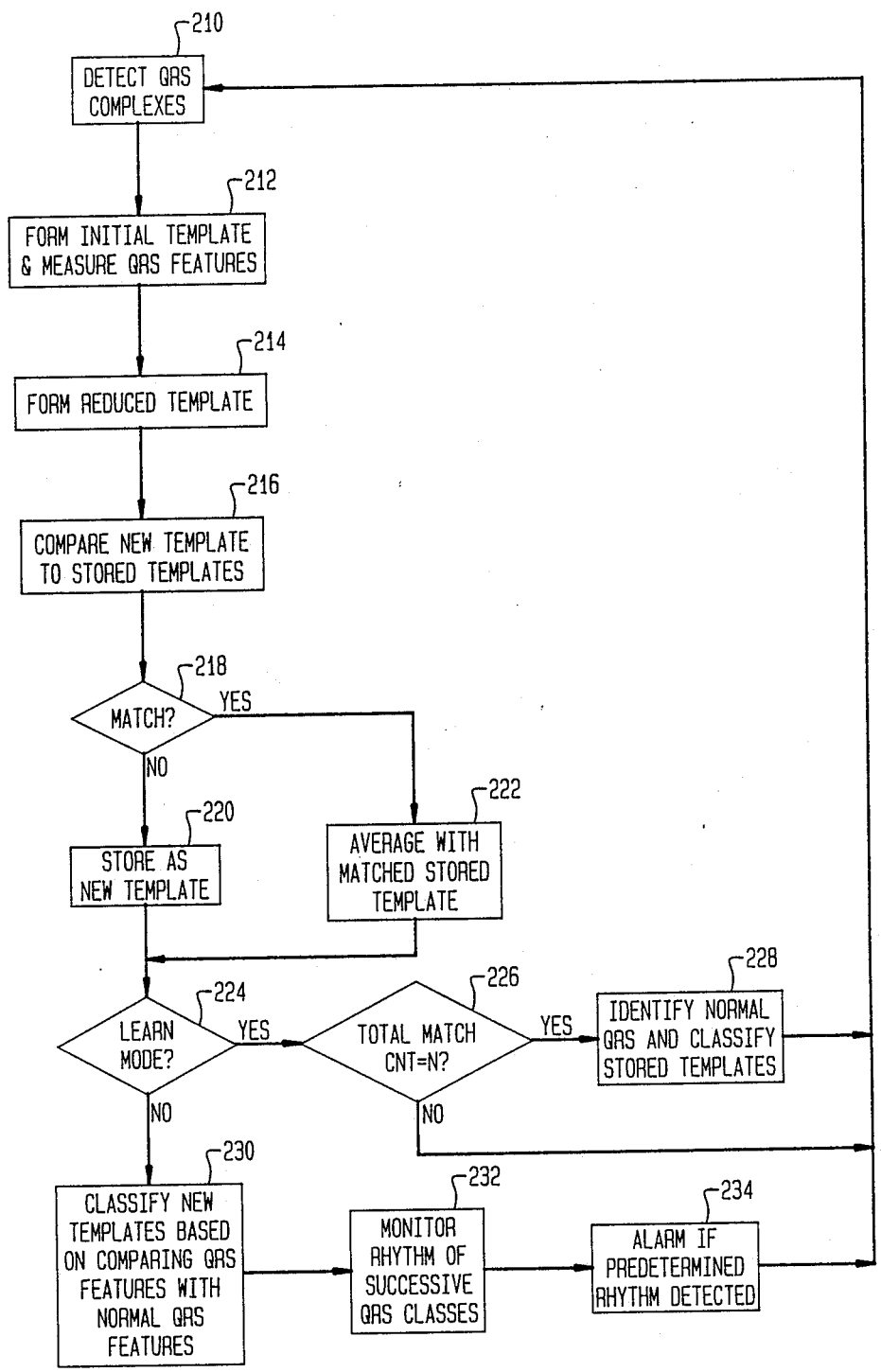
FIG. 3 illustrates a simplified flow diagram of the operation of the monitor of FIG. 1.

The flow-chart of FIG. 3 illustrates in more detail the operation of the heart monitor of FIG. 1. Initially, the first QRS complex is detected, a reduced template is formed and then stored in a buffer memory 22 (steps 210–214). Since this is the first template, there will be no match with a previously stored template, and the initial template is stored in a first template storage position in reduced template memory 26 (steps 216–220). Furthermore, the previously measured QRS features are also stored with its respective template at this time. These features will be used later to classify the stored templates as normal or abnormal. Successive QRS complexes are similarly processed to form new reduced templates which are presented as candidates to comparator 24 and compared with those reduced templates already stored therein. If the comparison shows a match with one of the stored templates, the elements, as well as the feature values of the candidate reduced template are averaged with the values of the template it matched (step 222). If there is no match, the candidate reduced template is stored as a new reduced template. This process continues for the number of QRS complexes which define a "learn mode." In the present example, the learn mode continues until one of the template storage locations of memory 26 has had 10 matches. At that time, the stored templates and their features are processed to define one of them as normal and thereafter, its features are used as a comparison basis to classify the templates stored in memory 26 as normal or abnormal (steps 224–228). Thereafter, as shown by steps 230–234, successive candidate templates are classified as normal or abnormal by comparison of their features with those defined as normal (after matching, step 222) and the rhythm detector provides an alarm whenever e.g., a specified sequence of normal and abnormal QRS complexes are detected.

There has thus been shown and described novel apparatus for comparing waveshape portions of a time varying waveform which fulfills all the objects and advantages sought therefor. Many changes, modifications, variations and other uses and applications of the subject invention will, however, become apparent to those skilled in the art after considering this specification and the accompanying drawings which disclose a preferred embodiment thereof. For example, the arrhythmia detector incorporating the present invention could be only a portion of a more generalized cardiac monitor. Additionally, it is not necessary that the initial template be normalized before forming the reduced template. Furthermore, the number of samples in the reduced template can be changed and other types of combinations of the samples of the initial template can be used for forming each sample of the reduced template e.g., combinations involving addition, subtraction, multiplication or division. It should also be noted that the comparison of the reduced template can be accomplished by means other than the simple measure of similarity used in the preferred embodiment. For example, one could use conventional correlation techniques. Finally, it should be clear that a substantial portion of the FIG. 1 arrangement could be embodied by software processing rather than discrete hardware elements. All such changes, modifications, variations and other uses and applications which do not depart from the spirit and scope of the invention are deemed to be covered by the invention which is limited only by the claims which follow.

What I claim is:

1. A method for comparing sequential waveshape portions of at least one time-varying signal, comprising:
    forming sequential initial templates, each initial template consisting of a plurality of digital signal sample values representative of the amplitude of successive time-spaced samples of a respective portion of said time-varying signal;
    forming from each of said initial templates a corresponding reduced template having a plurality of digital signal elements which is less in number than the plurality of sample values in its corresponding initial template, each element of said reduced template comprising a combination of at least two sample values from its corresponding initial template; and
    processing correspondingly positioned elements of at least two of said reduced templates for deriving a comparison signal representative of the degree of similarity of the respective portions of said time-varying signal represented by said at least two reduced templates.

2. The method of claim 1, wherein said step forming sequential initial templates includes:
    normalizing of the digital signal sample values of said initial templates by assigning first and second predetermined values to the maximum and minimum valued digital signal sample values, respectively, of said initial templates.

3. The method of claim 1, wherein said step forming said reduced templates comprises:
    successively subtracting different pairs of said digital signal sample values, which pairs of sample values are representative of the amplitude of said time-spaced samples of said time-varying signal which are spaced apart by a time equalling the time between successive time-spaced samples multiplied by one-half the total number of sample values contained in said initial templates, for forming rach element of said reduced templates.

4. The method of claim 1, wherein said processing step comprises:
summing the result of successive subtractions of correspondingly positioned elements within respective ones of said reduced templates, for deriving said comparison signal representative of the degree of similarity of said respective waveshape portions.

5. The method of claim 4, further including:
comparing said comparison signal to a threshold level and indicating a match of said waveshape portions represented by said reduced templates when said comparison signal does not exceed said threshold level.

6. Apparatus for comparing waveshape portions of at least one time-varying signal, comprising:
means for forming sequential initial templates, each initial template consisting of a plurality of digital signal sample values representative of the amplitude of successive time-spaced samples of a respective portion of said time-varying signal;
means for forming from each of said initial templates a corresponding reduced template having a plurality of digital signal elements which is less in number than the plurality of sample values in its corresponding initial template, each element of said reduced template comprising a combination of at least two sample values from its corresponding initial template; and
means for processing correspondingly positioned elements of at least two of said reduced templates for deriving a comparison signal representative of the degree of similarity of respective portions of said time-varying signal represented by said at least two reduced templates.

7. Apparatus according to claim 6, wherein said means for forming said initial templates includes:
means for normalizing the digital signal sample values of said initial templates by assigning first and second predetermined values to maximum and minimum valued digital signal sample values, respectively, of said initial templates.

8. Apparatus according to claim 6, wherein said means for forming said reduced templates comprises:
means for successively subtracting different pairs of said digital signal sample values, which pairs of sample values are representative of the amplitude of said time-spaced samples of said time-varying signal which are spaced apart by a time equalling the time between successive time-spaced samples multiplied by one-half the total number of sample values contained in said initial templates, for forming each element of said reduced templates.

9. Apparatus according to claim 6, wherein said means for processing comprises:
means for summing and means for subtracting for summing the result of successive subtractions of correspondingly positioned elements within respective ones of said reduced templates, for deriving said comparison signal representative of the degree of similarity of said respective waveshape portions.

10. Apparatus according to claim 9, further including:
means for comparing said comparison signal to a threshold level; and
means for indicating a match of said waveshape portions represented by said reduced templates when said comparison signal does not exceed said threshold level.

11. Apparatus for monitoring electrocardiograph (ECG) signals, comprising:
electrodes for developing an analog ECG signal;
A/D conversion means for developing digital ECG signal sample values representative of the amplitude at sequential time-spaced intervals of said analog ECG signals;
means for forming successive initial templates consisting of said digital signal sample values for successive portions of said ECG signal;
means for combining at least two digital signal sample values of each initial template for forming each element of a corresponding reduced template;
means for processing corresponding positioned elements of at least two of said reduced templates for deriving a comparison signal representative of the degree of similarity of successive time-spaced intervals of said ECG signal represented by said at least two reduced templates.

12. Apparatus according to claim 11, wherein said means for forming successive initial templates includes:
means for normalizing the digital signal sample values of said initial templates by assigning first and second predetermined values to maximum and minimum valued digital signal sample values, respectively, of said initial templates.

13. Apparatus according to claim 11, wherein said means for combining comprises:
means for successively subtracting different pairs of said digital signal sample values of said initial templates, which pairs of sample values are representative of the amplitude of said time varying signal at given time-spaced intervals, the spacing between said given intervals being determined by multiplying the time between successive intervals with one-half the total number of sample values contained in said initial templates, for forming each element of said reduced templates.

14. Apparatus according to claim 11, wherein said means for processing comprises:
means for summing and means for subtracting for summing the result of successive subtractions of correspondingly positioned elements within respective ones of said reduced templates, for deriving said comparison signal representative of the degree of similarity of successive portions of said ECG signal.

15. Apparatus according to claim 14, further including:
means for comparing said comparison signal to a threshold level; and
means for indicating a match of said successive portions of said ECG signal represented by said reduced templates when said comparison signal does not exceed said threshold level.

* * * * *